US012569334B2

(12) United States Patent
Kozin et al.

(10) Patent No.: US 12,569,334 B2
(45) Date of Patent: Mar. 10, 2026

(54) WINGED GRAFTS FOR TYMPANIC MEMBRANE REPAIR AND AUGMENTATION

(71) Applicants: Massachusetts Eye and Ear Infirmary, Boston, MA (US); President and Fellows of Harvard College, Cambridge, MA (US)

(72) Inventors: Elliott Kozin, Boston, MA (US); Aaron K. Remenschneider, Boston, MA (US); Nicole Black, Shelby Township, MI (US)

(73) Assignees: Massachusetts Eye and Ear Infirmary, Boston, MA (US); President and Fellows of Harvard College, Cambridge, MA (US)

( * ) Notice: Subject to any disclaimer, the term of this patent is extended or adjusted under 35 U.S.C. 154(b) by 1109 days.

(21) Appl. No.: 17/607,983

(22) PCT Filed: May 1, 2020

(86) PCT No.: PCT/US2020/031100
§ 371 (c)(1),
(2) Date: Nov. 1, 2021

(87) PCT Pub. No.: WO2020/223663
PCT Pub. Date: Nov. 5, 2020

(65) Prior Publication Data
US 2022/0346945 A1 Nov. 3, 2022

Related U.S. Application Data

(60) Provisional application No. 62/842,044, filed on May 2, 2019.

(51) Int. Cl.
*A61F 2/18* (2006.01)
*A61L 27/36* (2006.01)
(Continued)

(52) U.S. Cl.
CPC ............ *A61F 2/18* (2013.01); *A61L 27/3641* (2013.01); *A61L 27/38* (2013.01); *A61L 27/54* (2013.01);
(Continued)

(58) Field of Classification Search
CPC .. A61F 2/18; A61F 2002/183; A61F 2002/18; A61F 2/0063; A61F 2002/0068; A61B 2017/00606; A61B 17/12168
See application file for complete search history.

(56) References Cited

U.S. PATENT DOCUMENTS

| | | | |
|---|---|---|---|
| 4,014,971 A | 3/1977 | Perkins | |
| 4,744,792 A * | 5/1988 | Sander | A61F 11/202 623/10 |

(Continued)

FOREIGN PATENT DOCUMENTS

| | | | |
|---|---|---|---|
| CN | 2162943 | 4/1994 | |
| EP | 3270821 B1 * | 8/2020 | A61F 2/18 |

(Continued)

OTHER PUBLICATIONS

Translation of JP H06233792 A (Year: 1994).*
(Continued)

*Primary Examiner* — Melanie R Tyson
*Assistant Examiner* — Paris Marie Blass
(74) *Attorney, Agent, or Firm* — Fish & Richardson P.C.

(57) ABSTRACT

The disclosure relates to winged graft devices, methods of manufacture, and methods of use to repair, e.g., repair perforations, in tympanic membranes, or to augment defective tympanic membranes.

19 Claims, 3 Drawing Sheets

(51) Int. Cl.
  *A61L 27/38* (2006.01)
  *A61L 27/54* (2006.01)
(52) U.S. Cl.
  CPC . *A61F 2002/183* (2013.01); *A61F 2210/0076* (2013.01); *A61F 2230/0006* (2013.01); *A61F 2240/001* (2013.01); *A61L 2300/412* (2013.01); *A61L 2420/02* (2013.01); *A61L 2420/08* (2013.01); *A61L 2430/14* (2013.01)

(56) References Cited

U.S. PATENT DOCUMENTS

| | | | |
|---|---|---|---|
| 5,007,934 | A | 4/1991 | Stone |
| 5,501,700 | A | 3/1996 | Hirata |
| 6,309,419 | B1 | 10/2001 | de Juan, Jr. et al. |
| 8,197,433 | B2 | 6/2012 | Cohen |
| 8,480,610 | B1 | 7/2013 | Hill |
| 9,149,295 | B1 | 10/2015 | Condon |
| 9,987,168 | B2 | 6/2018 | Fritsch |
| 10,786,349 | B2 | 9/2020 | Remenschneider et al. |
| 10,799,341 | B2 | 10/2020 | Remenschneider et al. |
| 2003/0018291 | A1 | 1/2003 | Hill et al. |
| 2005/0075733 | A1 | 4/2005 | D'Eredita |
| 2006/0142736 | A1 | 6/2006 | Hissink et al. |
| 2007/0082052 | A1 | 4/2007 | Bonassar et al. |
| 2008/0234817 | A1 | 9/2008 | Huettenbrink et al. |
| 2008/0268016 | A1 | 10/2008 | Fang et al. |
| 2009/0240330 | A1* | 9/2009 | Steinhardt ................. A61F 2/18 623/10 |
| 2011/0245929 | A1* | 10/2011 | Rakin ....................... A61F 2/08 606/228 |
| 2012/0191030 | A1 | 7/2012 | Avior |
| 2013/0345722 | A1 | 12/2013 | Margulis |
| 2014/0012282 | A1 | 1/2014 | Fritsch |
| 2014/0094910 | A1 | 4/2014 | Steinhardt et al. |
| 2014/0155934 | A1 | 6/2014 | Baxter et al. |
| 2014/0194891 | A1 | 7/2014 | Shahoian |
| 2014/0257518 | A1 | 9/2014 | McAlpine et al. |
| 2014/0303728 | A1 | 10/2014 | Steinhardt et al. |
| 2017/0367893 | A1 | 12/2017 | Loushin et al. |
| 2018/0042718 | A1 | 2/2018 | Remenschneider et al. |
| 2018/0263763 | A1 | 9/2018 | Margulis et al. |
| 2021/0315556 | A1* | 10/2021 | de Poix ................. A61L 31/005 |

FOREIGN PATENT DOCUMENTS

| | | | | |
|---|---|---|---|---|
| JP | S50-031693 | | 3/1975 | |
| JP | H06233792 A | * | 8/1994 | |
| JP | 2011-110204 A | | 6/2011 | |
| WO | WO 2011/142425 | | 11/2011 | |
| WO | WO-2013148839 A1 | * | 10/2013 | ........... A61F 2/0063 |
| WO | WO-2014163840 A1 | * | 10/2014 | ........... A61B 17/068 |
| WO | WO 2016/005946 | | 1/2016 | |
| WO | WO 2016/154148 | | 9/2016 | |
| WO | WO 2018/053087 | | 3/2018 | |

OTHER PUBLICATIONS

AU Office Action in AU Application No. 2016235333, dated Jan. 15, 2020, 5 pages.

Barry III et al., "Direct-Write Assembly of 3D Hydrogel Scaffolds for Guided Cell Growth. Advanced Materials," 2009, 21:2407-10.

Boedts et al., "A scanning electron-microscopic study of different tympanic grafts," Am J Otol, 1990, 11(4):274-7.

Calobrace, "The design and engineering of the Memory Shape breast implant." Plast Reconstr Surg, 2014, 134(3 Suppl): 10S-15S.

Cheng et al., "Motion of the surface of the human tympanic membrane measured with stroboscopic holography," Hear Res, 2010, 263(1-2):66-77.

Cheng et al., "Wave motion on the surface of the human tympanic membrane: holographic measurement and modeling analysis," J Acoust Soc Am, 2013, 133(2):918-37.

Cranford et al., "Nonlinear material behaviour of spider silk yields robust webs," Nature, 2012, 482(7383):72-6.

Decraemer et al., "Shape and derived geometrical parameters of the adult, human tympanic membrane measured with a phase-shift moire interferometer," Hear Res, 1991, 51(1):107-21.

Dvorak, et al., "Repair of chronic tympanic membrane perforations with long-term epidermal growth factor," Laryngoscope, 1995, 105(12 Pt 1): 1300-1304.

Ensari, "Effects of polylactic acid film on middle ear mucosa and cochlear function in Guinea pigs," Eur Arch Otorhinolaryngol, 2015, 272(5): 1091-1097.

EP Extended Search Report in European Appln. No. 16769523.8, dated Oct. 25, 2018, 8 pages.

EP Extended Search Report in European Appln. No. 17851503.7, dated Sep. 9, 2019, 7 pages.

EP Office Action in Appln. No. 17851503.7, dated Sep. 30, 2019, 8 pages.

Fernandes, "Composite chondroperichondrial clip tympanoplasty: The 1-6, 7/1-7/6 triple "C" technique," Otolaryngology Head Neck Surgery, 2003, 128: 267-72.

Geckil et al., "Engineering hydrogels as extracellular matrix mimics," Nanomedicine (Lond), 2010, 5(3):469-84.

Gersdorff, et al., "Overlay versus underlay tympanoplasty. Comparative study of 122 cases," Rev Laryngol Otol Rhinol (Bord), 2003, 124(1): 15-22.

Ghanem, et al., "Butterfly cartilage graft inlay tympanoplasty for large perforations," Laryngoscope, 2006, 116(10): 1813-1816.

Gratson et al., "Microperiodic structures: direct writing of three-dimensional webs," Nature, 2004, 428(6981):386.

Hanson Shepherd et al., "3D Microperiodic Hydrogel Scaffolds for Robust Neuronal Cultures," Adv Funct Mater, 2011, 21:47-54.

Hardman et al., "Tympanoplasty for Chronic Tympanic Membrane Perforation in Children: Systematic Review and Meta-analysis," Otol Neurotol. 2015, 36(5):796-804.

Hiraide et al., "The fiber arrangement of the pathological human tympanic membrane," Arch Otorhinolaryngol, 1980, 226(1-2):93-9.

Hod et al., "Inlay "butterfly" cartilage tympanoplasty," Am J Otolaryngol, 2013, 34(1): 41-43.

Hong et al., "Repair of tympanic membrane perforation using novel adjuvant therapies: a contemporary review of experimental and tissue engineering studies," Int J Pediatr Otorhinolaryngol, 2013, 77(1): 3-12.

House et al., "Incus homografts in chronic ear surgery," Arch Otolaryngol, 1966, 84(2):148-53.

International Preliminary Report on Patentability in International Appln. No. PCT/US2020/031100, dated Nov. 2, 2021, 7 pages.

International Search Report and Written Opinion in International Appln. No. PCT/US2020/031100, dated Aug. 4, 2020, 9 pages.

Jang et al., "Regeneration of chronic tympanic membrane perforation using 3D collagen with topical umbilical cord serum," International Journal of Biological Macromolecules, 2013, 62: 232-240.

JP Office Action in Japanese Appln. No. 2017-549395, dated Jan. 7, 2020, 15 pages (with English translation).

Kaylie et al., "Revision chronic ear surgery," Otolaryngol Head Neck Surg, 2006, 134(3):443-50.

Khanna and Tonndorf, "Tympanic membrane vibrations in cats studied by time-averaged holography," J Acoust Soc Am, 1972, 51:1904-20.

Kim et al., "Functional and Practical Outcomes of Inlay Butterfly Cartilage Tympanoplasty." Otol Neurotol, 2014, 35: 1458-1462.

Kohn et al., "New perspectives in myringoplasty," Int J Artif Organs, 1984, 7(3):151-62.

Kozin et al., "Design, fabrication, and in vitro testing of novel three-dimensionally printed tympanic membrane grafts," Hear Res, Oct. 2016, 340: 191-203.

Kozin et al., Theoretical and Practical Considerations of 3-Dimensionally Printed Biomimetic Tympanic Membrane Grafts: Preliminary Design, Manufacture, and Acoustic Testing. Middle Ear Mechanics and Research In Otology, 2015, M. Gaihede. Aalborg, Denmark, MEMRO, 3 pages.

Levin et al., "Preliminary results of the application of a silk fibroin scaffold to otology," Otolaryngology—Head and Neck Surgery, Mar. 2010, 142(3_suppl):S33-5.

(56)                    References Cited

OTHER PUBLICATIONS

Levin et al., "Grafts in myringoplasty: utilizing a silk fibroin scaffold as a novel device," Expert Rev Med Devices, 2009, 6(6):653-64.

Lewis, "Direct Ink Writing of 3D Functional Materials," Advanced Functional Materials, 2006, 16:2193-204.

Lim, "Structure and function of the tympanic membrane: a review," Acta oto-rhino-laryngologica Belgica, 1995, 49(2):101-15.

Lukasiak et al., "Biodegradation of Silicones (Organosiloxanes)," 2005, 52 pages.

Marquet, "Human middle ear transplants," J Laryngol Otol, 1971, 85(6):523-39.

Minoda et al., "External auditory canal stenting utilizing a useful rolled, tapered silastic sheet (RTSS) post middle ear surgery," Auris Nasus Larynx, 2010, 37(6):680-684.

Mironov et al., "Organ printing: computer-aided jet-based 3D tissue engineering," Trends in Biotechnology, 2003, 21(4):157-61.

Mota et al., "Multiscale fabrication of biomimetic scaffolds for tympanic membrane tissue engineering," Biofabrication, May 2015, 7: 025005.

Murphy and Atala, "3D bioprinting of tissues and organs," Nat Biotechnol, 2014, 32(8):773-85.

Nadol et al., "Cellular immunologic responses to cochlear implantation in the human," Hear Res, 2014, 318: 11-17.

Parekh et al., "Repair of the tympanic membrane with urinary bladder matrix," Laryngoscope, 2009, 119(6): 1206-1213.

Park et al., "Predictors for outcome of paper patch myringoplasty in patients with chronic tympanic membrane perforations," Eur Arch Otorhinolaryngol, 2015, 272(2): 297-301.

PCT International Preliminary Report on Patentability in international Application No. PCT/US2016/023482, dated Jun. 20, 2016, 9 pages.

PCT International Preliminary Report on Patentability in international Application No. PCT/US2017/051501, dated Mar. 19, 2019, 8 pages.

PCT International Search Report and Written Opinion in International Application No. PCT/US16/23482, mailed on Jun. 20, 2016, 10 pages.

PCT International Search report and Written Opinion in International Application No. PCT/US2017/051501, mailed on Nov. 29, 2017, 14 pages.

Pfaltz and Griesemer, "Pericard: a new biometerial for tympanoplasty: preliminary report," Am J Otolaryngol, 1985, 6(3):266-8.

Qin et al., "Structural optimization of 3D-printed synthetic spider webs for high strength. Nature communications," 2015, 6:7038.

Rosowski et al., "Computer-assisted time-averaged holograms of the motion of the surface of the mammalian tympanic membrane with sound stimuli of 0.4-25 kHz," Hear Res, 2009, 253(1-2):83-96.

Rosowski et al., "New data on the motion of the normal and reconstructed tympanic membrane," Otol Neurotol. 2011, 32(9):1559-67.

Seliktar, "Designing cell-compatible hydrogels for biomedical applications," Science, 2012, 336(6085):1124-8.

Seyyedi and Nadol, Jr., "Intracochlear Inflammatory Response to Cochlear Implant Electrodes in Humans," Otol Neurotol, 2014, 35: 1545-1551.

Shimada and Lim, "The fiber arrangement of the human tympanic membrane. A scanning electron microscopic observation," Ann Otol Rhinol Laryngol, 1971, 80(2):210-7.

Sun et al., "Direct-Write Assembly of 3D Silk/hydroxyapatite Scaffolds for Bone Co-Cultures," Advanced Healthcare Materials, 2012, 1:729-35.

Tamimi et al., "Osseointegration of dental implants in 3D-printed synthetic onlay grafts customized according to bone metabolic activity in recipient site," Biomaterials, 2014, 35(21): 5436-5445.

Teh et al., "Tissue Engineering of the 2-12,14 Tympanic Membrane," Tissue Engineering Part B: Reviews, Apr. 1, 2013, 19(2): 116-32.

Tonndorf and Khanna, "The role of the tympanic membrane in middle ear transmission," Ann Otol, 1970, 79:743-53.

Tonndorf and Khanna, "Tympanic-membrane vibrations in human cadaver ears studied by time-averaged holography," J Acoust Soc Am, 1972, 52:1221-33.

Uebersax et al., "Biocompatibility and osteoconduction of macroporous silk fibroin implants in cortical defects in sheep," Eur J Pharm Biopharm, 2013, 85(1):107-18.

Ulku et al., "Comparisons of the mechanics of partial and total ossicular replacement prostheses with cartilage in a cadaveric temporal bone preparation," Acta Otolaryngol, 2014, 134(8):776-84.

Villar-Fernandez et al., "Outlook for tissue engineering of the tympanic membrane," Audiology Research, Jan. 2015, 5: 117.

Weber et al., "Tissue-engineered calcium alginate patches in the repair of chronic chinchilla tympanic membrane perforations," Laryngoscope, 2006, 116(5): 700-704.

Wehrs, "Grafting techniques," Otolaryngol Clin North Am, 1999, 32(3): 443-455.

Wieland et al., "Poly(glycerol sebacate)-engineered plugs to repair chronic tympanic membrane perforations in a chinchilla model," Otolaryngol Head Neck Surg, 2010, 143(1): 127-133.

Wrzeszcz, et al., "Hydrogel coated and dexamethasone releasing cochlear implants: quantification of fibrosis in guinea pigs and evaluation of insertion forces in a human cochlea model," J Biomed Mater Res B Appl Biomater, 2015, 103(1): 169-178.

Zhang and Gan, "A comprehensive model of human ear for analysis of implantable hearing devices," IEEE Trans Biomed Eng, 2011, 58(10):3024-7.

* cited by examiner

WINGED GRAFTS FOR TYMPANIC MEMBRANE REPAIR AND AUGMENTATION

CLAIM OF PRIORITY

This application is a national stage entry of International Patent Application No. PCT/US2020/031100, filed on May 1, 2020, and claims priority to U.S. Provisional Patent Application No. 62/842,044 filed on May 2, 2019, and entitled "WINGED GRAFTS FOR INCISION-FREE REPAIR OF TYMPANIC MEMBRANE PERFORATIONS," the entirety of which is incorporated herein by reference.

TECHNICAL FIELD

This invention relates to methods and devices for the repair or augmentation of the tympanic membrane.

BACKGROUND

Diseases of the middle ear, such as chronic suppurative otitis media (CSOM), are common in children and adults. CSOM affects more than 30 million individuals worldwide annually. The most frequent long-term complication in patients with CSOM is persistent tympanic membrane (TM) perforation and conductive hearing loss. Perforations of the TM can also be caused by trauma, including blast trauma or barotrauma, or as a complication from tympanostomy tube placement. Such TM perforations result in considerable morbidity, including hearing loss, pain, recurrent infections, and decreased quality of life.

These complications are surgically correctable via myringoplasty or tympanoplasty, which are common procedures, but can take several hours, require an operating room, and typically require general anesthesia. Myringoplasty is the closure of a perforation of the TM, and when myringoplasty is combined with ossicular reconstruction, the procedure is called tympanoplasty. The goals of both procedures are to recreate a robust barrier between the canal and middle ear, as well as to reestablish sound transmission to the ossicular chain in a fashion similar to the native TM. Autologous materials such as fascia and cartilage that are harvested at the time of surgery can be challenging to manipulate and place due to their mechanical properties and lack of design features to enable them to be held in place in the TM perforation. Materials must maintain their position following surgical placement to ensure successful results. Healing times following these surgical procedures range between 4-8 weeks and wound healing results are highly variable.

This results in the need for repeat surgery in up to 40% of cases. During typical eardrum repair, the middle ear and external auditory canal are often packed with surgical dressings, which also reduce hearing during the hearing process. Inadequate outcomes are also often due to displacement of grafts during the healing process and/or poor approximation of grafts to the perforation and remnant TM. Graft failure may result in pain, hearing loss, otorrhea, dizziness, and persistent ear infections and the need for revision surgery.

SUMMARY

The disclosure is based, at least in part, on the discovery that one can prepare new winged graft devices as disclosed herein to repair and/or augment TMs, e.g., to repair perforations, using novel methods of manufacture and, in-office procedures, without the need for general anesthesia or incisions in the patient to harvest graft material.

In one aspect, the disclosure provides winged graft devices for use in repairing or augmenting a TM, including a first graft material layer; and a second graft material layer, wherein each of the first and second graft material layers have a shape, e.g., a geometric shape, e.g., a circle or square or other configuration, or a shape to correspond to a perforation in the TM or to a missing or damaged, e.g., overly elastic or scarred, portion of a TM of a subject, wherein each of the first and second graft material layers have at least one elongated radial slit, e.g., one or more slits cut, formed, or molded into the material, wherein each slit extends from an outer perimeter or edge of the geometric shape of the graft material layer towards a center of the layer. If there are two or more slits, the slits do not reach the center of the graft material layer, but leave a bridge of graft material between the two or more slits at about the center of each layer. The centers or the bridges of material in the first and second graft material layers are connected to form a winged graft device including at least first and second medial wings, which form an underlay portion of the graft, and at least first and second lateral wings, which form an overlay portion of the graft. The bridge may also be slightly offset from a central point, e.g., to permit better interdigitation of the two graft layers.

The winged graft devices enable what is known as an "underlay graft" procedure, which is the standard of care in TM perforation repairs, to be done through the perforation without the need for any surgical access to the middle ear and without the need for any packing material in the middle ear. The new winged graft devices enable a medical provider to place the underlay portion of the graft device (the medial wings of the device) through the perforation and the outer (lateral) wings of the device form the overlay portion of the device that holds the underlay portion (the medial wings) up against the medial surface of the TM to permit cells to grow in and heal the TM, and thus provide a stable underlay repair without the need for packing in the middle ear to hold the graft in place.

In other examples, the new winged graft devices can be used to augment hearing, for example, in patients in which their TM is overly elastic or compliant, thickened, or infected, scarred by tympanosclerosis, thickened or thinned due to disease, replaced by scar tissue, mucosalized, or otherwise abnormal, or wherein the patient has myringosclerosis, and the winged graft device is designed to augment the tympanic membrane. While the graft devices can be used for replacement of a portion of a missing TM, they can also be used to replace a defective, but intact TM. In these situations, medial lobes of the winged graft devices that form an underlay portion of the graft can have enhanced stiffness, e.g., with elements in the form of radial and/or concentric ribs that provide enhanced stiffness to the medial lobes, and thus to the TM as well.

If there are specific regions of the TM that are intact, but damaged, such as through myringosclerosis or tympanosclerosis, the damaged areas can also be removed and replaced. In other examples, the new winged graft devices can be used to deliver biological agents such as growth factors, antibiotics, anti-inflammatory agents, steroids, and the like to the TM or middle ear space. For example, a patient experiencing chronic otitis media with an otherwise intact TM could receive a device that enables a steroid and/or antibiotic mixture to elute into the middle ear space, either in conjunction with a tympanostomy tube being placed or on its own. The device could also help enable closure of the perforation following tympanostomy tube removal.

In some implementations of these graft devices, the centers or bridges of graft material are connected by inter-digitating the first graft material layer and the second graft material layer by sliding a slit of the first graft material layer into a slit of the second graft material layer until the center or bridge of material of the first graft material layer contacts the center or bridge of material in the second graft material layer to connect the first and second graft material layers. The centers or bridges can also be connected using a weld, adhesive, a polymer, e.g., a thermoset or UV-cured polymer, a thermoplastic material, a suture, or a mechanical connection.

Examples of polymers that can be used to bridge the two centers or bridges include silicones, polyurethanes, fluoroplastics, nylon, polyethylene terephthalate, polycarbonate, acrylonitrile butadiene styrene, poly(p-phenylene oxide), polybutylene terephthalate, polypropylene, polyetheretherketone, polyethylene, polystyrene, polysulfone, polyvinylidene fluoride, polymethylmethacrylate, latex, polyacrylate, polyalkylacrylate, substituted polyalkylacrylate, polystyrene, poly(divinylbenzene), polyvinylpyrrolidone, poly(vinylalcohol), polyacrylamide, poly(ethylene oxide), polyvinylchloride, polyvinylidene fluoride, polytetrafluoroethylene, polydimethylsiloxane (PDMS), hyaluronic acid (HA), poly(glycolic acid) (PGA), poly (lactic-co-glycolic acid) (PLGA), polylactic acid (PLA), poly(ester urethane) urea (PEUU), poly(carbonate urethane) urea (PECUU), and mixtures thereof.

In various implementations, the bridges of graft material in both the first and second graft material layers are sufficiently small, or are connected in such a way, to enable the first and second graft material layers to be rotated with respect to each other such that the slits in the first graft material layer do not overlap the slits in the second graft material layer.

In some embodiments, each of the first and second graft material layers includes one or more slits, e.g., two, three, or more, slits to form two or more wings. If there are two slits in each graft material layer, the first medial wing of the winged graft device includes a first half of the first graft material layer, the first lateral wing of the winged graft device includes a second half of the first graft material layer, the second medial wing of the winged graft device includes a first half of the second graft material layer, and the second lateral wing of the winged graft device includes a second half of the second graft material layer.

In various embodiments of the winged graft devices, the first and second graft material layers are made of the same material. The first and second graft material layers can also be fabricated in one piece. Alternatively, each of the graft material layers can be made of two (or more) different materials, wherein a first half of a graft material layer, e.g., which forms the medial wing of the graft material layer is made of a more robust material, e.g., a material that biodegrades more slowly (or not at all) compared to a material used to form a second half of the layer that forms the lateral wing. In other embodiments, the first half of the layer that forms the medial wing of each graft material layer includes stiffening ribs in a radial pattern, e.g., extending from bridge of material, and/or concentric pattern centered around the bridge. In these embodiments, the two medial wings form an underlay that can be used to stiffen an overly elastic TM.

In some implementations, the devices further include one or more biological agents or materials, e.g., a cellular adhesion and a cell invasion-inducing material, e.g., a growth factor, e.g., any one or more of a fibroblast growth factor (FGF), a vascular endothelial growth factor (VEGF), a platelet-derived growth factor (PDGF), a keratinocyte growth factor (KGF), a transforming growth factor (TGF) beta, an epidermal growth factor (EGF), or platelet rich plasma. The devices can also or alternatively further include one or more cells, e.g., fibroblasts, chondrocytes, keratinocytes, stem cells, progenitor cells, mesenchymal cells, endothelial cells, platelets, and epithelial cells. For example, the cells can be harvested from the patient or from different sources, e.g., a transplant from another subject or from cultured cell lines. The devices can also further include one or more antibiotics, steroids, small molecules, cytokines such as IL-10, chemokines, proteins, and biologics, e.g., in the form of drug eluting materials that slowly release such agents.

In various implementations, the winged graft devices can be animal derived, for example, collagen sheets, gelatin, silk, porcine or bovine tissues (e.g., submucosa, pericardium, or fascia), ALLODERM® (human dermal regenerative tissue matrix), DuraMatrix® (collagen biologic), DuraGen® (collagen biologic), absorbable gelatin, elastin, GELFOAM® (water-insoluble, nonelastic, porous, pliable sponge matrix product prepared from purified porcine skin, gelatin granules and water for injection), BIODESIGN® otologic repair graft (water-insoluble nonelastic porous pliable product prepared from purified porcine skin, gelatin, and water), dural matrix, extracellular matrix, temporalis fascia, perichondrium, pericranium, and mucosa.

In other implementations, they can be plant derived (e.g., cellulose paper), or a synthetic material, such a as a polymer. Some examples of polymers include silicones, polyurethanes, fluoroplastics, nylon, polyethylene terephthalate, polycarbonate, acrylonitrile butadiene styrene, poly(p-phenylene oxide), polybutylene terephthalate, polypropylene, polyetheretherketone, polyethylene, polystyrene, polysulfone, polyvinylidene fluoride, polymethylmethacrylate, latex, polyacrylate, polyalkylacrylate, substituted polyalkylacrylate, polystyrene, poly(divinylbenzene), polyvinylpyrrolidone, poly(vinylalcohol), polyacrylamide, poly(ethylene oxide), polyvinylchloride, polyvinylidene fluoride, polytetrafluoroethylene, polydimethylsiloxane (PDMS), hyaluronic acid (HA), poly(glycolic acid) (PGA), poly (lactic-co-glycolic acid) (PLGA), polylactic acid (PLA), poly(ester urethane)urea (PEUU), poly(carbonate urethane) urea (PECUU), and mixtures thereof.

The different layers can be made of the same or of different materials, and the lateral wings can all be made of the same or different materials, and the medial wings can all be made of the same or different materials, which can be the same or different from the material of the lateral wings.

The winged graft devices can have an outer diameter of about 2 to 12 millimeters, e.g., 3, 4, 5, 6, 7, 8, 9, 10, or 11 mm, e.g., based on a size of a perforation in, or damaged portion of, a TM of a patient. The first and second graft material layers can have a thickness of 10 to 750 micrometer, e.g., 25, 50, 75, 100, 125, 150, 175, 200, 250, 300, 400, 500, 600, or 750 micrometers.

In various implementations, the winged graft devices can be permeable to air, impermeable to air, and/or selectively permeable to one or more drugs or other agents including small molecules, biologics, steroids, and antibiotics, and impermeable to water. For example, the lateral wings of the two layers of a winged graft device could be made to be permeable or selectively permeable to air and liquids such as biological agents or materials, to provide nourishment to the growing layer of skin forming beneath the overlay portion of the graft device. The devices can also be made permeable to air to aid in the equalization of middle ear pressure, particularly when a patient has Eustachian tube dysfunction.

In another aspect, the disclosure features methods of repairing or augmenting a TM, e.g., repairing a perforation, e.g., in a subject, e.g., a human patient or a mammal, e.g., a domesticated mammal such as a cat, dog, horse, cow, primate, or elephant, to heal or augment a damaged TM. The methods include obtaining a winged graft device as described herein, e.g., as illustrated in FIGS. 1A to 1D; applying the winged graft device to a lateral surface of the TM with medial wings contacting the lateral surface of the TM; manipulating the medial wings of the winged graft device through the perforation or other opening in the TM to enable the medial wings to contact a medial surface of the TM; and arranging and flattening the lateral wings of the winged graft device to contact the lateral surface of the TM, thereby securing the graft device to the TM and enabling the medial wings to become secured to the medial surface of the TM.

In these methods, the TM is secured between the lateral wings on the lateral side of the TM and the medial wings on the medial side of the TM, e.g., without need of any packing material within the inner ear to hold the medial wings in place against the medial surface of the TM. The interlocking nature of the winged graft permit stabilization against the remnant TM and immediate improvement in hearing.

In certain embodiments, the methods further include applying a vasoconstrictive agent to the ear canal and TM and/or applying an anesthetic agent, e.g., viscous lidocaine, to the ear canal and TM, and optionally filling the ear canal with an antibiotic agent after the perforation is closed with the winged graft device.

In another aspect, the disclosure features methods of fabricating a winged graft device as described herein, e.g., as illustrated in FIGS. 1A to 1D. The methods include forming or obtaining a first graft material layer; forming or obtaining a second graft material layer, wherein each of the first and second graft material layers have a geometric shape, e.g., a circle, or a shape to correspond to (e.g., overlap on all sides) a perforation or opening created in a TM of a subject, and wherein the first and second graft material layers can be formed in one piece or as two separate pieces; forming, e.g., cutting or molding, one or more slits, e.g., 2 or 3, or more slits, in each of the first and second graft material layers that extend from edges, e.g., opposed edges when there are two slits, of the layers towards a center of each layer, leaving a center or bridge of graft material, for example, at about the center of each layer between the slits; and fastening the two centers or bridges of graft material to each other to connect the first and second graft material layers and form a winged graft device having at least first and second medial wings and at least first and second lateral wings.

In some of the methods, the two centers or bridges are fastened by interdigitating the first and second graft material layers, e.g., by sliding a slit of the first graft material layer into a slit of the second graft material layer until the center or bridge of material of the first graft material layer contacts the center or bridge of material of the second graft material layer. In some embodiments, the contact alone can hold the two graft material layers together.

In some embodiments of these methods, the two centers or bridges of material are formed as one piece and are thus fastened to each other during manufacture. In other embodiments, the two bridges are fastened to each other by an adhesive, by application of heat, e.g., a weld, a glue, a polymer, a suture, or by a mechanical connection element.

In some embodiments, the bridge of material in both of the first and second graft material layers is sufficiently small, or are fastened in such a way, to enable the first and second graft material layers to be rotated with respect to each other such that the slits in the first graft material layer do not overlap the slits in the second graft material layer.

In certain implementations, each of the first and second graft material layers comprises two slits and two wings, and wherein the first medial wing of the winged graft device comprises a first half of the first graft material layer, wherein the first lateral wing of the winged graft device comprises a second half of the first graft material layer, wherein the second medial wing of the winged graft device comprises a first half of the second graft material layer, and wherein the second lateral wing of the winged graft device comprises a second half of the second graft material layer. In these embodiments, the first and second medial wings together for an underlay portion of the graft device and the first and second lateral wings together for an overlay portion of the graft device.

In some implementations, the methods can further include storing the winged graft device in a saline solution or a solution containing therapeutic molecules, such as growth factors. In other implementations, the methods can further include seeding the winged graft device with cells, or wherein the winged graft material is a tissue including cells or cellular elements or platelets, and storing the cell-containing winged graft device in a culture medium under culturing conditions to maintain the living cells.

In some embodiments, the methods further include sterilizing the winged graft device, for example, the devices can be sterilized chemically (e.g., using formaldehyde), by radiation, by heat, by ultraviolet irradiation, by plasma treatment, by ethylene oxide gas, gamma irradiation, or e-beam irradiation.

In another aspect, the disclosure provides methods of fabricating the winged graft devices described herein by injection molding or 3D printing the winged graft device in one piece, including the one or more slits in each layer.

In another aspect, the disclosure includes kits that include two or more of the winged graft devices described herein, wherein the kit includes at least two of the winged graft devices in two or more different sizes and/or two or more different shapes. In addition, the kit can include devices made of different materials. The kits can also include other components, such as one or more biological agents or materials, e.g., an anesthetic agent, a vasoconstrictive agent, and an antibiotic agent. The kits can come either fully assembled or as an unassembled device (e.g., two separate layers) with instructions for assembly.

The kits can also include surgical instruments or tools used to implant the new graft devices, e.g., curved needles, such as a Rosen needle, or other tools to manipulate the graft device into place, or to create an opening in the TM, and/or to roughen the surface of the TM before implanting the winged graft device. The kits can be packaged, e.g., with all components in one package, and sterilized, e.g., a single, sterile package.

The winged graft devices can further include at least one of a cellular adhesion-inducing material and a cellular invasion-inducing material. The devices can also include one or more living cells, such as living fibroblasts, chondrocytes, keratinocytes, and/or epithelial cells, in a scaffold material that enables the cells to thrive and reproduce once implanted.

The new winged TM graft devices can be prepared easily and can be used to repair TM perforations, including central, partial, subtotal, or total perforations. These two-layered winged graft devices include at least two medial wings designed to adhere to the medial or under side of the TM facing the middle ear, and at least two lateral wings that are secured on top (lateral surface) of the TM facing the external ear canal. The two graft material layers are interdigitated to connect them across two bridges of graft material in the two layers, to secure the winged graft device such that the TM surrounding the perforation and surrounding healthy TM tissue is sandwiched between the two graft material layers of the winged graft device to promote wound repair and ensure proper biological environmental milieu. Closure of the perforation enables immediate hearing improvement.

The new winged graft devices and methods minimize the morbidity of traditional approaches to TM repair and augmentation, eliminate the need for general anesthesia, and maintain high surgical success rates. In addition, the new winged graft devices and methods provide an in-office technique that applies the surgical principles of an underlay graft using an off the shelf or autologous material without the need for an operating room or general anesthesia. When the new winged graft devices are made of synthetic materials or non-autologous, e.g., porcine tissues (e.g., porcine submucosa, porcine pericardium, bovine fascia, bovine pericardium), tissues, they eliminate the need for autologous surgical graft harvest, saving time and patient morbidity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A shows the TM and the perforation, as visualized through an endoscope. FIG. 2B shows the placement of a winged graft device with forceps directly through the ear canal on the surface of the TM. FIG. 2C shows the process of shifting the lower wings or flanges of the winged graft through the perforation and into place behind (medial to) the TM using a curved needle. FIG. 2D shows the final position of the graft, with two wings below or medial to the TM and two wings above or outside the TM. The winged grafts remain connected to each other through the initial construction of the device to permit stable closure of the TM perforation without need for packing material.

FIG. 3A shows the TM and the perforation, as visualized through an endoscope. FIG. 3B shows the placement of a graft device and positioning of the wings with a needle. FIG. 3C shows the final position of the graft device. FIG. 3D shows the healed TM with robust vascular ingrowth at 3 months.

Like reference symbols in the various drawings indicate like elements.

DETAILED DESCRIPTION

Winged Graft Devices

Figures 1A, 1B, 1C, 1D:
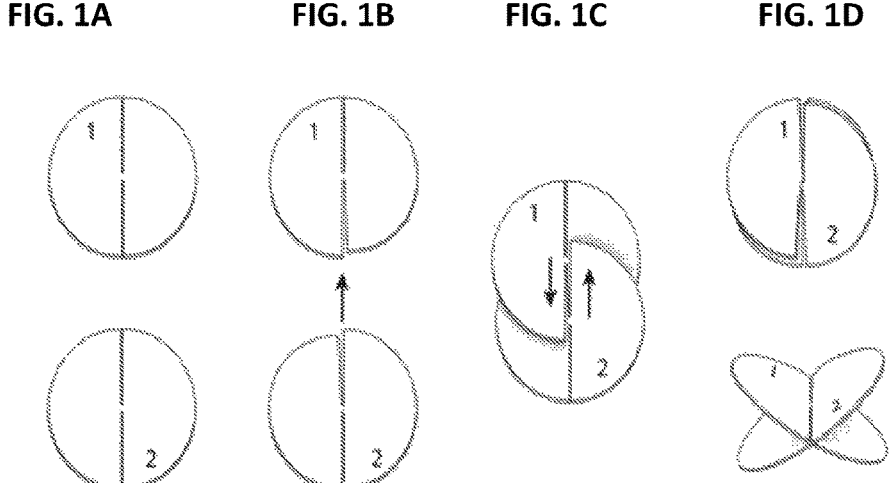
FIGS. 1A to 1D are a series of schematic representations of the steps to construct a winged graft device as described herein starting with two disks of graft material. While in this figure the two pieces of graft material are circular, they can be a different geometric configuration, such as a square, pentagon, hexagon, etc.

In general, two pieces of a graft material are interdigitated to create a "winged" graft with four "wings" that allows for simultaneous lateral and medial grafting in one, simple procedure. The two pieces of graft material (1 and 2 in FIGS. 1A-D) can be the same or different graft materials. The graft material or materials used to make the assembled winged graft device 10 as shown in FIG. 1D can include any graft material appropriate for use in tympanoplasty used now or discovered in the future. TM grafts typically consist of autologous temporalis fascia, perichondrium, cartilage, and/or skin grafts. Thus, these materials can include organic tissue such as those harvested from the patient or a different donor. One of the benefits of the present winged graft devices is that they can be made of graft materials from non-autologous materials, for example, porcine submucosa material or artificial grafts, in advance of the procedure, without the need for tissue harvest from the patient. Winged grafts of different sizes could be assembled into a kit to permit the surgeon to select the appropriate sized winged graft for TM repair.

In some embodiments, each piece or layer of the graft device can be made of two or more different materials. For example, each layer, e.g., disk, could have two halves, each made of a different material, e.g., each having a different biodegradation rate. For example, the two medial wings that together for the underlay portion of the device may be made of a material that may biodegrade slower (or not at all) compared to the material used to make the two lateral wings that together form the overlay part of the graft device. In this way, the overlay portion of the graft device can be designed to biodegrade more rapidly than the underlay portion, allowing the epithelial surface of the lateral side of the TM to form and heal over the original perforation more quickly, without being hindered by the overlay portion of the graft device.

In some embodiments, the thickness of the different wings can be designed to be different. For example, the graft material, e.g., Biodesign® (porcine small intestinal submucosa) can be thinner for the lateral wings. Thus, different polymers or materials can be used for the medial and lateral wings, but also different thicknesses can be used for the medial and lateral wings. For instance, a graft material can be used for each graft material layer, or one half of each graft material layer, that is a first thickness, and the second layer can be a second, different thickness, wherein the thinner layer will biodegrade and bioresorb faster.

In addition, either or both of the underlay portion and the overlay portion of the graft device can either degrade or remain permanently adhered to the TM, depending on the nature of the repair or augmentation. For example, if the underlay portion of the graft device is designed to augment an overly elastic TM, then there may be a benefit to keeping the underlay graft device in place permanently.

Artificial graft materials can include one or more biodegradable materials, e.g., materials in which the rate of biodegradation can be selected before implantation. For example, the graft materials can include or be made of at least one or more of polydimethylsiloxane (PDMS), hyaluronic acid (HA), poly(glycolic acid) (PGA), poly (lactic-co-glycolic acid) (PLGA), polylactic acid (PLA), polyurethane, poly(ester urethane)urea (PEUU), poly(carbonate urethane) urea (PECUU), collagen, fibrin, nylon, silk, polycaprolactone, porcine or bovine tissues (e.g., submucosa, pericardium, or fascia), ALLODERM® (regenerative tissue matrix), DuraMatrix® (collagen biologic), DuraGen® (collagen biologic), absorbable gelatin, elastin, GELFOAM® (water-insoluble, nonelastic, porous, pliable product prepared from purified porcine skin, gelatin, and water), dural matrix, or other medical grade synthetic materials.

The graft materials can themselves include or be treated with biological agents or materials, e.g., to aid in the healing of the TM after graft placement, such as those described below. For example, the graft devices can include one or more of a cellular adhesion and/or a cell invasion-inducing material, e.g., growth factors. The growth factors can include, e.g., a fibroblast growth factor (FGF), vascular endothelial growth factor (VEGF), platelet-derived growth factor (PDGF), transforming growth factor (TGF) beta, and a keratinocyte growth factor (KGF). In some embodiments, the winged grafts can be soaked in the patient's own or donated serum, blood, or platelet rich plasma, either before or during the implantation procedure.

The winged graft devices can further include one or more drug eluting materials that can elute drugs such as antibiotics, steroids, small molecules, cytokines (e.g., interleukins 2, 4, 6, 10), chemokines, and biologics. The devices can further include one or more cells, e.g., fibroblasts, chondrocytes, keratinocytes, stem cells, progenitor cells, and epithelial cells, or cellular elements such as platelets, which exist naturally in the graft material, or are introduced to the graft material.

Storage conditions need to be appropriate for the materials used for the devices and the liquid medium in which they are stored. The appropriate temperature, either warm or cold, depends upon the components used in the devices. For example, if the devices contain living cells, the devices would be stored in a growth medium at typical cell culturing conditions and temperatures. Alternatively, the graft materials can also be allografts that can be harvested at the time of the procedure and can be prepared as described herein without the need for storage.

Methods of Fabrication of Winged Graft Devices

In one embodiment, under sterile conditions, a punch, e.g., a biopsy punch having a diameter of 3, 4, 5, 6, 7, 8, 9, 10 mm or larger (e.g., for large mammals), is used to cut two biologic graft material layer "disks" from a sheet of graft material. The disks for the winged graft devices can also be fashioned using other sharp instruments or by laser or other forms of machine-controlled cutting. The disks can be cut or fabricated in a round, square, triangular pattern, or any other shape that best corresponds to the TM perforation to be repaired or opening created for TM augmentation. The size depends on the size of the TM perforation or opening, and thus the present disclosure includes kits of two or more winged graft devices having two or more different diameters that are available as "off-the-shelf" components that are made in advance of any given TM perforation repair procedure and stored until use. In general, the two layers of the graft device should both overlap the perforation or opening around the entire periphery.

As shown in the particular example in FIG. 1A, once the two graft material disks or other shapes are cut from a sheet of graft material, two linear, radial, e.g., approximately axial, cuts or slits are made or formed, e.g., cut, at opposite edges or sides, e.g., at the 12 o'clock and 6 o'clock positions, extending towards the center of the disk, leaving a small "bridge" of graft material between the two slits at about the center of each layer that prevents a complete bisection of the graft layer disk and holds the two wings of the graft material disk together. Note that in other embodiments, one can also make three or four (or more) cuts or slits to create three or four (or more) wings in each disk, and the cuts or slits need not be straight lines, but can be curved, wavy, or zig-zag. In addition, if the separate layers of the graft device are molded or 3D printed, the slit can be formed during manufacture rather than being cut into the layers.

The bridge of material can be between 0.05 and 0.6 mm, but should typically not be larger than about 0.6 mm for use in most human patients. Bridges larger than 0.6 mm have an inability to be fashioned appropriately into a winged graft and may limit the ability for a TM repair or augmentation in human patients. However, winged grafts for perforations or openings in TM of larger mammals may require larger disks, with appropriately sized bridges that still permit the manipulation of the wings, e.g., up to about 1 to 2 mm or more.

As shown in FIGS. 1B and 1C, after creating two graft material disks or layers with the appropriate slits, the disks are interdigitated, creating a "winged" graft, with four sets of flanges or "wings" in two planes (medial and lateral). As shown in FIG. 1D, when viewed from the side in a "X" configuration, the two disks are arranged and connected such that one lateral "wing" of each disk 1, 2, is located above a horizontal plane that cuts through the X configuration (and represents the TM), and one medial wing of each disk is located below the horizontal plane. In FIG. 1D, disk 1 has one lateral wing on the left above the horizontal plane, and one medial wing on the right below the horizontal plane. Disk 2 has one lateral wing on the right above the horizontal plane, and one medial wing on the left below the horizontal plane.

Once the two disks are connected as described above, one can also optionally rotate the top disk with respect to the bottom disk, e.g., 10, 15, 20, 25, 30, 35, 40, or 45 degrees, so that the slits in the top layer of graft material do not overlap the slits in the bottom layer of graft material. This ensures that there will be no slits that pass all the way through both disks, and provides a complete seal on both the medial and lateral surface of the TM, especially in the area of the perforation or opening, ensuring a robust closure. Rotating the disks after fashioning the winged graft helps to ensure its stability in the post-operative setting.

Once prepared, the winged graft device is stored, e.g., in sterile saline or culture medium if live cells are included. If there are no living cells, prefabricated disks can also be sterilized either chemically (e.g., using formaldehyde) or by radiation or heat using standard techniques. Once the devices are sterilized, living cells can be introduced using sterile techniques.

In other embodiments, winged graft devices as shown in FIGS. 1A-1D can also be prefabricated from one piece or two pieces of graft material, e.g., by injection molding as a single piece using a liquid graft material that hardens (by a change in temperature, pH, or other parameters) to form the disks, stamping, punching, or otherwise cutting, two pieces of graft material and gluing, welding, stapling, or otherwise connecting the two layers at the respective central bridge areas, or by 3D printing a single piece of graft material having the configuration shown in the figures. Important aspects of such prefabricated devices include that they have two layers that are connected in the middle by a small bridge area of the material (such that the wings can be individually manipulated, that each layer has at least two separate wings or flanges (e.g., one can have 2, 3, 4, or more wings per layer/disk) connected only by the centrally located bridge of material (that permits rotation of the top and bottom disks as well as manipulation of the wings to push them through the TM perforation), and that the cuts that create the separate wings do not overlap so that the two disks of the device can completely seal the TM perforation.

Methods of Implanting Winged Graft Devices

Patients are typically placed in the supine position in a clinic setting and are awake throughout the procedure. The new winged graft devices and procedures disclosed herein are ideal for in-office settings, but can also be carried out in an operating room, e.g., with a sedated or anesthetized patient.

After cleaning the ear with a disinfectant, e.g., betadine, sterile cotton balls soaked in an anesthetic, e.g., viscous lidocaine, are inserted to fill the ear canal (EAC). Further local anesthetic liquid, e.g., 1% lidocaine, and a vasocon-strictive agent, such as epinephrine, can then be instilled in the ear canal skin as an injection, e.g., at three points around the meatus.

Figure 2A:
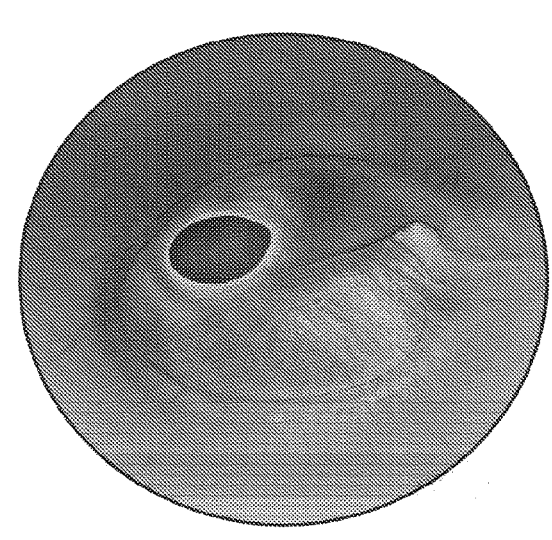
FIGS. 2A to 2D are a series of schematic representations of the steps to repair a TM perforation using one of the new winged graft devices described herein.

Using an endoscopic telescope, e.g., a rigid Hopkins rod endoscopic telescope (Karl Storz, Tuttlingen, Germany), to visualize the TM, a needle, e.g., a Rosen needle, and forceps, e.g., an alligator forceps, can optionally be used to freshen the margins around the perforation with an instrument to remove the rim around the perforation producing a raw circumferential edge of cells of the remaining eardrum. FIG. 2A shows a perforation on the left side of a TM as portrayed in this figure after this rimming procedure has been done. The winged graft may also be placed without rimming of the perforation although outcomes are generally not as favor-able.

Figure 2B:
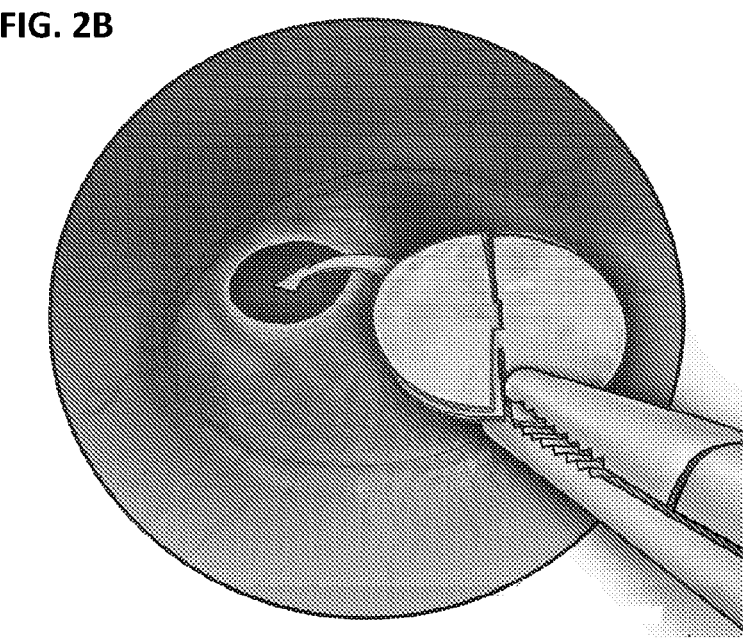

The endoscopic telescope is then re-introduced into the tympanic cavity to inspect the middle ear. A cotton ball soaked in a vasoconstrictive agent, e.g., 1:100,000 epineph-rine is placed on the TM. As shown in FIG. 2B, a winged graft device is grasped, e.g., with forceps, and placed directly on the lateral surface of the TM and the two medial wings (one from each disc) are placed through the perfora-tion with lateral wings resting on the TM surface. No packing is placed into the middle ear, thus the sound conducting system is not dampened and the patient is not at risk for developing a caloric response from changes in temperature in the middle ear from packing.

Figure 2C:
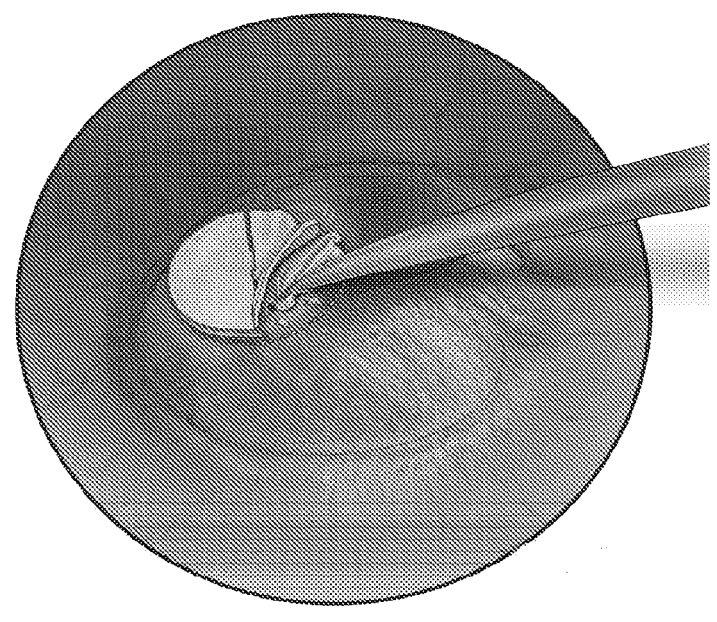

As shown in FIG. 2C, using a needle, e.g., a Rosen needle, the two medial wings touching the TM are inserted medially through the perforation in the TM, while the lateral two wings remain lateral to (on top of) the TM. The wings are also manipulated to ensure that they remain rotated with respect to each other so that the cuts in the top and bottom disks do not overlap.

Figure 2D:
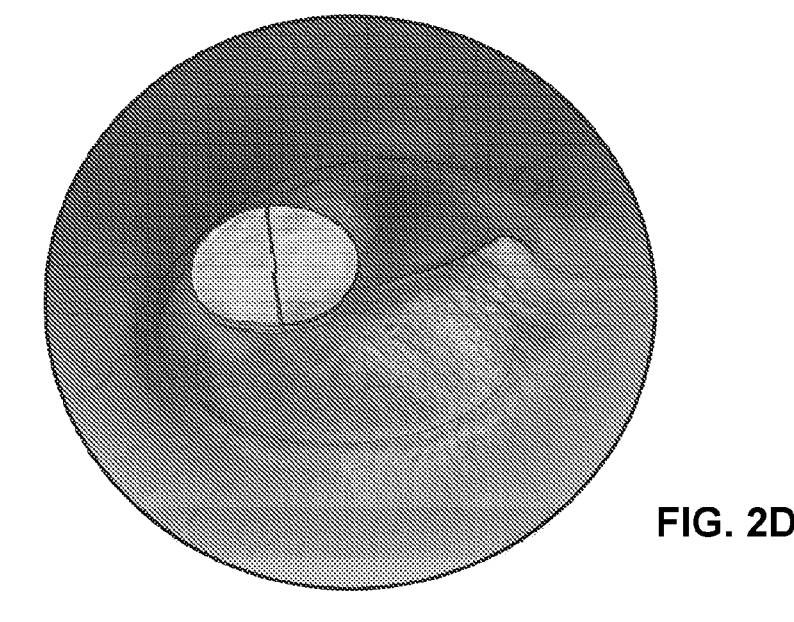

As shown in FIG. 2D, at the conclusion of the placement, the two lateral wings of the winged graft device remain visible on the outer (lateral) surface of the TM. They may be slightly rotated to ensure complete closure of the perforation or opening. Next, one or more absorbable gelatin sponges soaked in an antibiotic suspension are placed lateral to the graft. No gelatin sponge or packing is required in the middle ear, which is a significant benefit to the patient. Patients have an immediate boost to their hearing, which is notable. The ear canal is then filled with an antibiotic ointment, such as bacitracin ointment.

In general, any remaining packing of the outer ear is removed at about fourteen days post-operatively at the first post-operative clinic visit. The new methods and devices provide healing within about two weeks and hearing returns to baseline within four weeks. This is a significant improve-ment for patients compared to typical operating room TM perforation repairs.

EXAMPLES

The invention is further described in the following examples, which do not limit the scope of the invention described in the claims.

Example 1

Human Patient Study

The novel winged graft devices described herein have been used to reconstruct the TM successfully in 18 ears of sixteen patients. A study of the effectiveness of the winged graft devices described herein was carried out in 16 patients. The average size of the TM perforations was 4.0 mm (range 2-7 mm). The procedures were conducted in-office, without general anesthesia, and required no incisions.

Figures 3A, 3B, 3C, 3D:
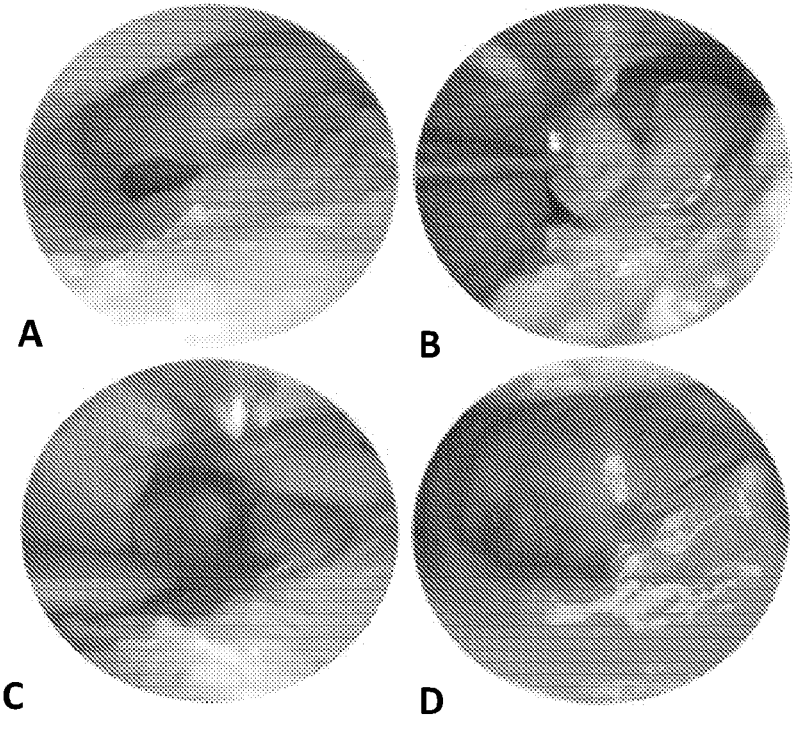
FIGS. 3A-3D are representations of photographic images of a TM perforation repair in a human patient using a winged graft device as described herein and illustrated in FIGS. 1A to 1D.

Patients were placed in the supine position in the clinic setting and were awake throughout the procedure. After cleaning the ear with betadine, sterile cotton balls soaked in viscous lidocaine were inserted to fill the ear canal (EAC). Four mL of 1% lidocaine with epinephrine 1:100,000, was then instilled at three points around the meatus. Using a 3 mm, 14 cm rigid Hopkins rod endoscopic telescope (Karl Storz, Tuttlingen, Germany) to visualize the TM, a Rosen needle and alligator were used to rim the perforation. The perforation in the TM is shown in FIG. 3A. The endoscope was introduced into the tympanic cavity to inspect the middle ear. A cotton ball soaked in 1:100,000 epinephrine was placed on the TM.

A winged graft as described herein was then held by an alligator forceps and placed directly on the lateral surface of the TM. As shown in FIG. 3B, using a Rosen needle, two flanges or wings (one from each disk of the graft device) touching the TM were inserted medial to the graft device, while the lateral two wings (one from each disk of the graft device) remain lateral to the TM.

As shown in FIG. 3C, after the conclusion of the place-ment of the winged graft device, the top (lateral) wings of the graft device were resting flat against the TM.

After placement of the winged graft device, absorbable gelatin sponges soaked in antibiotic suspension were placed lateral to the graft device. No gelatin sponge was used in the middle ear, but we filled the ear canal with bacitracin ointment.

Any remaining packing was removed fourteen days post-operatively at the first post-operative clinic visit.

The procedures were performed entirely under local anes-thetic, and took an average about 18.2 minutes (range 10-41 minutes), with a median of 15 minutes. We were able to complete the procedure in all patients attempted using only local anesthesia for the ear. No cases were aborted, which demonstrates the tolerability of the procedure to a variety of different patients. In addition, the new procedures described herein can be adapted for both small and large perforations and can be used successfully for both size conditions. These completed procedures demonstrate that the new methods and devices enable doctors to perform tympanoplasty procedures using the new devices in a much shorter period of time than such a procedure takes in the operating room, where times generally range from about 65 to about 180 minutes.

There were no complications in any of the patients, and 72% of perforations healed to complete closure of the TM within 2 weeks with clear evidence of vascular ingrowth to the graft (see FIG. 3D). We also found an improvement in air bone gap (ABG) in all patients with perforation closure. The average pre-operative hearing loss, as measured in ABG was 17.75 dB. Post-operatively, there was significant improvement with an ABG that was decreased to 7.64 dB, which indicates that hearing improved on average a total of 10 dB. As a reference, an improvement of 10 dB is perceived by the listener as hearing sounds twice as loud as they previously did, which is a statistically and clinically significant improvement. The mean duration of follow up was 15 weeks (range 6-24 weeks).

The population of patients was elderly and otherwise reticent to submit to general anesthesia for a traditional approach to TM repair. These findings support the concept that an endoscopic approach combined with a unique winged graft device as described herein permits in-office tympanoplasty without the disadvantages of general anesthesia, incisions to harvest graft material from the patient, and the need for a sterile operating room. These benefits are related to the novelty of the winged graft device design and the unexpected tolerance of the procedure, stability of repair, and high rate of success.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A winged graft device for use in repairing or augmenting a tympanic membrane having an opening, comprising
  a first graft material layer; and
  a second graft material layer,
  wherein each of the first and second graft material layers have a shape that corresponds generally to a shape of the opening in the tympanic membrane,
  wherein each of the first and second graft material layers has a size that extends beyond a perimeter of the opening in the tympanic membrane, and wherein the first and second graft material layers have the same, or about the same, outer diameter,
  wherein each of the first and second graft material layers has at least one radial slit that extends from an outer perimeter of the graft material layer towards a center of the graft material layer, wherein if there are two or more radial slits, the two or more slits do not touch, leaving a bridge of graft material at about the center of each graft material layer between the slits,
  wherein the two centers or bridges of graft material in the first and second graft material layers are connected to each other to form a winged graft device comprising at least first and second medial wings that together form an underlay portion of the winged graft device, and at least first and second lateral wings that together form an overlay portion of the winged graft device, and
  wherein the first graft material layer is rotated with respect to the second graft material layer such that the radial slit or slits in the first graft material layer do not overlap with the radial slit or slits in the second graft material layer such that there are no slits that pass all the way through the two graft material layers.

2. The device of claim 1, wherein the opening in the tympanic membrane is a perforation and the shape of the first and second graft material layers comprises a circular shape or other shape that corresponds generally to the shape of the perforation.

3. The device of claim 1, wherein the two centers or bridges of graft material are connected to each other by an adhesive or polymer, by application of heat, or by a mechanical connection element.

4. The device of claim 3, wherein the polymer comprises any one or more of polyurethane, polylactic acid, silicones, polyurethanes, fluoroplastics, nylon, polyethylene terephthalate, polycarbonate, acrylonitrile butadiene styrene, poly (p-phenylene oxide), polybutylene terephthalate, polypropylene, polyetheretherketone, polyethylene, polystyrene, polysulfone, polyvinylidene fluoride, polymethylmethacrylate, latex, polyacrylate, polyalkylacrylate, substituted polyalkylacrylate, polystyrene, poly(divinylbenzene), polyvinylpyrrolidone, poly(vinylalcohol), polyacrylamide, poly (ethylene oxide), polyvinylchloride, polyvinylidene fluoride, polytetrafluoroethylene, polydimethylsiloxane (PDMS), hyaluronic acid (HA), poly(glycolic acid) (PGA), poly (lactic-co-glycolic acid) (PLGA), polylactic acid (PLA), poly(ester urethane) urea (PEUU), or poly(carbonate urethane) urea (PECUU), or mixtures thereof.

5. The device of claim 1, wherein the two centers or bridges of graft material are connected to each other by interdigitating the first graft material layer and the second graft material layer by sliding a slit of the first graft material layer into a slit of the second graft material layer until the center or bridge of graft material of the first graft material layer contacts the center or bridge of graft material in the second graft material layer to connect the two centers or bridges of graft material in the first and second graft material layers.

6. A winged graft device for use in repairing or augmenting a tympanic membrane having an opening, comprising
  a first graft material layer; and
  a second graft material layer,
  wherein each of the first and second graft material layers have a shape that corresponds generally to a shape of the opening in the tympanic membrane,
  wherein each of the first and second graft material layers has a size that extends beyond a perimeter of the opening in the tympanic membrane, and wherein the first and second graft material layers have the same, or about the same, outer diameter,
  wherein each of the first and second graft material layers has at least two radial slits that extend from an outer perimeter of the graft material layer towards a center of the graft material layer to form two wings in each of the first and second graft materials, wherein the two or more slits do not touch, leaving a bridge of graft material at about the center of each graft material layer between the slits and the two wings,
  wherein the two centers or bridges of graft material in the first and second graft material layers are connected to each other to form a winged graft device comprising at least first and second medial wings that together form an underlay portion of the winged graft device, and at least first and second lateral wings that together form an overlay portion of the winged graft device, wherein the first medial wing of the winged graft device comprises a first wing of the first graft material layer, wherein the first lateral wing of the winged graft device comprises a second wing of the first graft material layer, wherein the second medial wing of the winged graft device comprises a first wing of the second graft material layer, wherein the second lateral wing of the winged graft device comprises a second wing of the second graft material layer, and wherein each of the two lateral wings and each of the two medial wings are all about the same size.

7. The device of claim 1, further comprising one or more of a cellular adhesion material and a cell invasion-inducing material.

8. The device of claim 1, further comprising one or more cells.

9. The device of claim 8, wherein the cells are harvested from the patient, from a transplant from another subject, or from cultured cell lines.

10. The device of claim 1, further comprising one or more antibiotics, steroids, small molecules, cytokines, chemokines, proteins, and biologics.

11. The device of claim 1, wherein the device comprises one or more of silicones, polyurethanes, fluoroplastics, polyethylene terephthalate, polycarbonate, acrylonitrile butadiene styrene, poly(p-phenylene oxide), polybutylene terephthalate, polypropylene, polyetheretherketone, polyethylene, polystyrene, polysulfone, polyvinylidene fluoride, polymethylmethacrylate, latex, polyacrylate, polyalkylacrylate, substituted polyalkylacrylate, polystyrene, poly(divinylbenzene), polyvinylpyrrolidone, poly(vinylalcohol), polyacrylamide, poly(ethylene oxide), polyvinylchloride, polyvinylidene fluoride, polytetrafluoroethylene, polydimethylsiloxane (PDMS), hyaluronic acid (HA), poly(glycolic acid) (PGA), poly (lactic-co-glycolic acid) (PLGA), polylactic acid (PLA), poly(ester urethane) urea (PEUU), poly (carbonate urethane) urea (PECUU), collagen, fibrin, nylon, silk, polycaprolactone, porcine or bovine tissues, human dermal regenerative tissue matrix, collagen, collagen biologic, absorbable gelatin, elastin, water-insoluble, nonelastic, porous, pliable materials prepared from porcine skin, gelatin, and water, dural matrix, extracellular matrix, temporalis fascia, perichondrium, pericranium, and mucosa.

12. The device of claim 1, wherein each graft material layer has an outer diameter of about 2.0 to about 12 millimeters and is sized to extend beyond an outer perimeter of the opening in the tympanic membrane.

13. The device of claim 1, wherein each of the first and second graft material layers has a thickness of 10 to 750 microns.

14. A method of repairing or augmenting a tympanic membrane having an opening, the method comprising obtaining a winged graft device of claim 1;

applying the winged graft device to a lateral surface of the tympanic membrane with medial wings contacting the lateral surface of the tympanic membrane;

manipulating the medial wings of the winged graft device through the opening to enable the medial wings to contact a medial surface of the tympanic membrane; and arranging and flattening the lateral wings of the winged graft device to contact the lateral surface of the tympanic membrane, thereby securing the graft device to the tympanic membrane and enabling the medial wings to become secured to the medial surface of the tympanic membrane.

15. The method of claim 14, wherein the tympanic membrane is secured between the lateral wings on the lateral side of the tympanic membrane and the medial wings on the medial side of the tympanic membrane without need of any packing material within the inner ear to hold the medial wings in place against the medial surface of the tympanic membrane.

16. The method of claim 14, further comprising applying a vasoconstrictive agent or an anesthetic agent, or both, to the ear canal and tympanic membrane, and optionally filling the ear canal with an antibiotic agent after the perforation is closed with the winged graft device.

17. The method of claim 14, further comprising creating the opening in the tympanic membrane before applying the winged graft device, wherein the tympanic membrane is overly elastic, thickened, or infected, scarred by tympanosclerosis, thickened or thinned due to disease, replaced by scar tissue, mucosalized, or otherwise abnormal, or wherein the patient has myringosclerosis, and the winged graft device is designed to augment the tympanic membrane.

18. A method of fabricating a winged graft device of claim 1, the method comprising:

forming or obtaining a first graft material layer;

forming or obtaining a second graft material layer, wherein each of the first and second graft material layers have a geometric shape, or a shape to match a perforation in a tympanic membrane of a subject, and wherein the first and second graft material layers can be formed in one piece or as two separate pieces;

forming one or more radial slits in each of the first and second graft material layers that extend from an outer perimeter of the graft material layer towards a center of the graft material layer, wherein if there are two or more radial slits, the two or more slits do not touch, leaving a bridge of graft material at about the center of each graft material layer between the slits; and fastening the two centers or bridges of graft material to each other to connect the first and second graft material layers and form a winged graft device comprising at least first and second medial wings that together form an underlay portion of the winged graft device, and at least first and second lateral wings that together form an overlay portion of the winged graft device.

19. The method of claim 18, wherein the two centers or bridges are fastened by interdigitating the first and second graft material layers by sliding a slit of the first graft material layer into a slit of the second graft material layer until the center or bridge of material of the first graft material layer contacts the center or bridge of material of the second graft material layer.

* * * * *